(12) United States Patent
Meyer et al.

(10) Patent No.: US 11,938,290 B2
(45) Date of Patent: Mar. 26, 2024

(54) SYSTEMS AND METHODS FOR DRAINING CEREBROSPINAL FLUID

(71) Applicant: Mayo Foundation for Medical Education and Research, Rochester, MN (US)

(72) Inventors: Fredric B. Meyer, Rochester, MN (US); Mohamed Bydon, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/140,050

(22) Filed: Apr. 27, 2023

(65) Prior Publication Data
US 2023/0364395 A1   Nov. 16, 2023

Related U.S. Application Data

(60) Provisional application No. 63/337,019, filed on Apr. 29, 2022.

(51) Int. Cl.
*A61M 27/00*  (2006.01)
*A61B 17/00*  (2006.01)
*A61F 2/01*   (2006.01)

(52) U.S. Cl.
CPC ....... *A61M 27/006* (2013.01); *A61B 17/0057* (2013.01); *A61F 2/01* (2013.01);
(Continued)

(58) Field of Classification Search
CPC .. A61M 2202/0478; A61M 2205/0238; A61M 2205/0266; A61M 2205/04;
(Continued)

(56) References Cited

U.S. PATENT DOCUMENTS 6,210,412 B1 * 4/2001 Michelson ............ A61F 2/4611
606/279
7,513,883 B2 4/2009 Glenn
(Continued)

OTHER PUBLICATIONS

Invitation to Pay Additional Fees, dated Jul. 10, 2023 for International Application No. PCT/US2023/020146.
(Continued)

*Primary Examiner* — Kai H Weng
(74) *Attorney, Agent, or Firm* — Wolf, Greenfield & Sacks, P.C.

(57) ABSTRACT

The present disclosure generally relates to systems and methods of use for draining cerebrospinal fluid (CSF) from a brain or a spinal canal in a subject, for example, to treat hydrocephalus or other conditions. In some embodiments, the disclosure relates to a device comprising a flow controller positioned within a conduit that allows CSF to flow through the conduit from a first end to a second end. This may allow the CSF to drain, for example, from an intradural space (such as a thecal sac) into, for example, a paraspinal space, paraspinal vein or other venous space, or peritoneal cavity. A variety of methods may be used to hold or anchor the device in place, for example, an expansion apparatus. In some embodiments, the device can be implanted percutaneously at a location along or within a subject's spinal column, thus reducing the need for surgery, general anesthesia, and hospitalizations.

22 Claims, 5 Drawing Sheets

(52) U.S. Cl.
CPC .... *A61F 2250/0051* (2013.01); *A61M 27/002* (2013.01); *A61M 2202/0464* (2013.01); *A61M 2205/0238* (2013.01); *A61M 2205/0266* (2013.01); *A61M 2205/04* (2013.01); *A61M 2205/3334* (2013.01)

(58) Field of Classification Search
CPC ........ A61M 2207/00; A61M 2210/125; A61M 27/002; A61F 2/01; A61F 2230/001; A61F 2230/0058; A61F 2250/0039; A61F 2250/0051; A61B 17/0057; A61B 17/0218; A61B 2017/00252; A61B 2017/00592; A61B 2017/00597; A61B 2017/00606; A61B 2017/00623; A61B 2017/0225; A61B 2017/0237
See application file for complete search history.

(56) References Cited

U.S. PATENT DOCUMENTS

| | | | |
|---|---|---|---|
| 2006/0206178 A1* | 9/2006 | Kim | A61B 17/3421 600/101 |
| 2007/0276390 A1* | 11/2007 | Solsberg | A61B 17/320016 606/79 |
| 2016/0136398 A1 | 5/2016 | Heilman et al. | |
| 2018/0256866 A1* | 9/2018 | Malek | A61M 27/006 |

OTHER PUBLICATIONS

Lee et al., Enhanced wall shear stress prevents obstruction by astrocytes in ventricular catheters. J R Soc Interface. Jul. 2020; 17(168):20190884. doi: 10.1098/rsif.2019.0884. Epub Jul. 1, 2020.
Whiteley et al., CSF opening pressure: reference interval and the effect of body mass index. Neurology. Nov. 14, 2006;67(9):1690-1. doi: 10.1212/01.wnl.0000242704.60275.e9.

* cited by examiner

SYSTEMS AND METHODS FOR DRAINING CEREBROSPINAL FLUID

RELATED APPLICATIONS

This application claims the benefit of U.S. Provisional Patent Application Ser. No. 63/337,019, filed Apr. 29, 2022, entitled "Systems and Methods for Draining Cerebrospinal Fluid," by Meyer, et al., incorporated herein by reference in its entirety.

FIELD

The present disclosure relates to systems and methods for draining cerebrospinal fluid in a subject.

BACKGROUND

Cerebrospinal fluid is routinely drained, or shunted, to treat a variety of illnesses, including, for example, hydrocephalus, pseudotumor cerebri, and idiopathic intracranial hypertension. Traditional shunting devices typically have a proximal catheter which is inserted into a brain ventricle or spinal thecal canal; a valve that controls spinal fluid drainage; and a distal catheter that is placed into a body space that can resorb the fluid (e.g., peritoneum, pleural space, or cardiac atrium). While effective, these devices often require general anesthesia and invasive surgeries for insertion and line placement. For example, traditional ventricular brain catheter systems require multiple incisions and burr holes through the skull for placement of the proximal catheters. Additional incisions are required across a subject's body to connect the proximal catheter to the valve and distal catheter for drainage, for example, in the peritoneum. This requires the subject to be admitted to a hospital and increases the risk of secondary infection. Accordingly, improvements in draining cerebrospinal fluid are needed.

SUMMARY

The present disclosure relates to systems and methods for draining cerebrospinal fluid in a subject. The subject matter of the present disclosure involves, in some cases, interrelated products, alternative solutions to a particular problem, and/or a plurality of different uses of one or more systems and/or articles.

In some embodiment, the disclosure relates to a device comprising an implantable structure defining a conduit therein connecting a first end to a second end, a flow controller positioned within the implantable structure in an orientation that allows fluid to flow through the conduit from the first end to the second end, a first expansion apparatus positioned at the first end of the implantable structure, wherein the expansion apparatus is expandable into an expanded configuration larger than the first end, and a second expansion apparatus positioned at the second end of the implantable structure, wherein the expansion apparatus is expandable into an expanded configuration larger than the second end.

Aspects of the disclosure relate to a device, comprising an implantable structure defining a conduit therein connecting a first end to a second end, a flow controller positioned within the implantable structure in an orientation that allows fluid to preferentially flow through the conduit from the first end to the second end, a first expansion apparatus comprising a plurality of first hinged arms each connecting a point on the first end of the conduit to a first common pivot, and a second expansion apparatus comprising a plurality of third hinged arms each connecting a point on the second end of the conduit to a third common pivot.

In some cases, the disclosure relates to a device, comprising an implantable structure defining a conduit therein connecting a first end to a second end, a flow controller positioned within the implantable structure in an orientation that allows fluid to preferentially flow through the conduit from the first end to the second end, a first expansion apparatus comprising a first expandable balloon positioned at least partially within the first end of the conduit, wherein the first expandable balloon comprises a first plurality of pores, and a second expansion apparatus comprising a second expandable balloon positioned at least partially within the second end of the conduit, wherein the second expandable balloon comprises a second plurality of pores.

In some embodiments, the disclosure relates to an apparatus, comprising a hollow needle shaft having a substantially constant cross-sectional area, a device at least partially contained within the hollow shaft, the device comprising, an implantable structure defining a conduit therein connecting a first end to a second end, a flow controller positioned within the implantable structure in an orientation that allows fluid to flow through the conduit from the first end to the second end, a first expansion apparatus positioned at a first end of the implantable structure, wherein the first expansion apparatus, when removed from the hollow needle shaft, is expandable into a configuration larger than the cross-sectional area of the hollow needle shaft, and a second expansion apparatus positioned at a second end of the implantable structure, wherein the second expansion apparatus, when removed from the hollow needle shaft, is expandable into a configuration larger than the cross-sectional area of the hollow needle shaft.

In some embodiments, the disclosure relates to a method, comprising injecting a hollow needle shaft having a substantially constant cross-sectional area and an implantable device at least partially contained within the hollow shaft into a subject, wherein the implantable device comprises a first expansion apparatus positioned at a first end of the implantable device, a second expansion apparatus positioned at a second end of the implantable device, and a flow controller positioned within the implantable structure in an orientation that allows fluid to flow through the conduit from the first end to the second end, expanding the first expansion apparatus into a configuration larger than the first end, at least partially withdrawing the needle shaft from the subject, and expanding the second expansion apparatus into a configuration larger than the second end.

Other aspects of the disclosure relate to a method of draining excess cerebrospinal fluid in a subject, wherein the subject has an intradural thecal sac containing excess cerebrospinal fluid and an extradural space proximate the intradural thecal sac, the method comprising: inserting an implantable structure defining a conduit therein into a subject to fluidly connect the intradural thecal sac to the extradural space, wherein the structure comprises a flow controller positioned in an orientation that allows the excess cerebrospinal fluid to flow through the conduit from the intradural thecal sac to the extradural space.

In another aspect, the present disclosure encompasses methods of making one or more of the embodiments described herein, for example, a device for draining fluid from a body cavity. In still another aspect, the present disclosure encompasses methods of using one or more of the embodiments described herein, for example, a device for draining fluid from a body cavity.

Other advantages and novel features of the present disclosure will become apparent from the following detailed description of various non-limiting embodiments of the disclosure when considered in conjunction with the accompanying figures.

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION

The present disclosure generally relates to systems and methods of use for draining cerebrospinal fluid (CSF) from a brain or a spinal canal in a subject, for example, to treat hydrocephalus or other conditions. In some embodiments, the disclosure relates to a device comprising a flow controller positioned within a conduit that allows CSF to flow through the conduit from a first end to a second end. This may allow the CSF to drain, for example, from an intradural space (such as a thecal sac) into, for example, a paraspinal space, paraspinal vein or other venous space, or peritoneal cavity. A variety of methods may be used to hold or anchor the device in place, for example, an expansion apparatus. In some embodiments, the device can be implanted percutaneously at a location along or within a subject's spinal column, thus reducing the need for surgery, general anesthesia, and hospitalizations.

Some aspects of the disclosure relate to systems and methods of implanting a device configured to shunt fluid from a first body cavity (e.g., thecal sac) to a second body cavity (i.e., drainage location) capable of receiving the fluid (e.g., peritoneum, extradural space, vein, etc.). For example, the fluid may be cerebrospinal fluid (CSF) from a brain or a spinal canal, which may be collecting in the thecal sac. It may be desirable to shunt the fluid into another location within the subject, e.g., to alleviate pressure. The fluid may be directed to a location where it can be resorbed by the body. Non-limiting examples include the epidural space, including fat and/or muscle, and/or vertebral bodies, and/or vasculature including the veins, such as the anterior and/or posterior spinal veins, or the like. While a variety of other shunt techniques have been suggested (e.g., lumboperitoneal shunts, ventriculoperitoneal shunts, ventriculoatrial shunts, etc.) they often require relatively long catheters or tubing, e.g., from inside the cranial cavity (in the head) to the lower abdomen, which can create a lot of difficulties or complications.

In contrast, in certain embodiments, methods and devices are provided that can result in shunting of fluids (e.g., CSF) over relatively short distances. For example, some embodiments are directed to an implantable device that can be used to shunt fluid, as discussed herein. Such devices can be implanted into a subject, via techniques such as percutaneous injection, optionally under fluoroscopic guidance, CT guidance, ultrasound guidance, etc. to aid in proper placement. In other embodiments, endoscopic guidance may be used for percutaneous placement. For example, the devices may be implanted at a location along or within the spinal column of the subject, e.g., to connect a first body cavity (e.g., a thecal sac or intradural space) to a second body cavity, or other location where fluid can be drained, e.g., soft tissues such as fat, muscle, bone, vasculature, or other locations such as discussed herein. A conduit within the device may thus allow fluid to flow from the first body cavity to the second body cavity, e.g., to relive fluid within the first body cavity.

The device may have any shape suitable for implanting, e.g., into the spinal column of a subject. For example, in some embodiments, the device is cylindrical. The device may comprise any suitable material, for example, polymers, metals, alloys, or the like. In addition, in some cases, the device may be contained within a hollow shaft, e.g., of a needle. The needle may be used to implant the device into the subject. In some embodiments, the needle may be inserted into a desired location, e.g., within the spinal column, and the device expelled from the needle and anchored into place as discussed herein. For instance, the needle may be withdrawn from the subject while leaving the device anchored within the subject.

In some embodiments, the device may be anchored or fixed in place after insertion, e.g., into the spine of a subject. For example, the device may have an expansion apparatus at one or more locations, which can be expanded (e.g., during insertion) to anchor or fix the device in place within the subject. For example, in one embodiment, a first end of a device may be placed or inserted into a first body cavity (e.g., a thecal cavity) and the first expansion apparatus expanded into a configuration larger than the first end, thus anchoring the first end of the device inside the subject. In some cases, the needle may be at least partially withdrawn from the subject. The device may be anchored in place, and thus may exit the needle as the needle is at least partially withdrawn. In addition, in some cases, a second expansion apparatus, located at a second end of the device, may be present to anchor the device once the needle is removed. For instance, in some embodiments, when the device exits the needle shaft, a second expansion apparatus may then be expanded into a configuration larger than the second end, thus anchoring the second end of the device, e.g., to a second body cavity, or other location where fluid can be drained, e.g., as discussed herein. The second expansion apparatus may expand spontaneously, or may be triggered (e.g., upon exiting, or afterwards). In addition, the second expansion apparatus may be the same or different than the first expansion apparatus.

A variety of expansion apparatuses may be used in various embodiments, which are discussed in further detail below. As mentioned, an expansion apparatus may anchor the device within the spinal column, e.g., within the spinal canal or vertebral body. As an example, the expansion apparatus may include a plurality of hinged arms, where the expansion apparatus is expandable into an expanded configuration larger than the first end, thus securing the device within the spinal canal. In some cases, the hinged arms may include a grapnel geometry, e.g., comprising an anchoring element, for example, a barb and/or a hook that can physically be embedded within the surrounding tissue. As another example, an expansion apparatus may include an expandable balloon. The expandable balloon may be expanded such that the balloon has, for example, a spherical shape or an elliptical shape, etc. In some embodiments, the expandable balloon may include spikes (e.g., to help anchor the device), and/or pores (for example, to allow fluid flow). As mentioned, in some cases, more than one expansion apparatus may be present within a device, including any of the ones described herein, and they may independently be the same or different.

In addition, in some embodiments, it may be desirable to prevent or limit the flow of fluids back from the second cavity to the first cavity. For instance, in some cases, the device may have a fluid flow controller to allow fluid to flow preferentially in one direction through the device, e.g., through a conduit within the device. For instance, the flow controller may allow cerebrospinal fluid to flow through the conduit from the first end (e.g., from a thecal sac) to the second end (e.g., to a paraspinal space or a peritoneal cavity), but inhibit or even prevent flow in the opposite direction. The flow controller may be any valve capable of regulating flow from the first end to the second end, for example, a one-way valve, or other configurations such as those described herein.

As mentioned, in some cases, the device may be contained within a hollow needle shaft that can be used to implant the device into the subject, e.g., percutaneously at a location along or within a subject's spinal column. For example, a device may be at least partially or fully contained within the hollow shaft of a needle. In some embodiments, the hollow needle shaft maintains the device in a collapsed configuration, wherein the collapsed configuration is smaller than the cross-sectional area of the hollow needle shaft (e.g., such that the device is positioned within the needle when in the collapsed configuration). In some embodiments, the needle may be used to place the device into a subject's body, e.g., via percutaneous injection. For example, the apparatus may be used to place the device in a subject's thecal sac, or in another location proximate the spinal column.

In certain cases, the device may have one, two or more expansion apparatuses that allow the device to be anchored within the subject. In some embodiments, for example, withdrawing the needle may allow a first expansion apparatus to expand into a configuration larger than the cross-sectional area of the hollow needle shaft. The expansion may occur spontaneously, e.g., as the device exits the hollow needle shaft, or the expansion may be triggered by a subsequent event. In addition, in some cases, further withdrawing the needle (e.g., after the first expansion apparatus has fully expanded) may allow a second expansion apparatus (if present) to expand into a configuration larger than the cross-sectional area of the hollow needle shaft. Such expansion may occur spontaneously or be triggered by a subsequent event. If more than one expansion apparatus is present within the device, they may independently be the same or different. In some embodiments, the hollow needle used for device insertion may be a portal component of an endoscopic device.

The above discussion is a non-limiting example of one aspect generally directed to systems and methods for draining cerebrospinal fluid. However, other embodiments are also possible besides those discussed above. Accordingly, and more generally, various aspects are directed to various systems and methods for draining cerebrospinal fluid, as discussed herein.

Certain aspects of the disclosure provide systems and methods for draining fluid from a first body cavity (e.g., thecal sac) to a second body cavity or space (e.g., paraspinal space or paraspinal vein), as needed to treat a subject suffering from, for example, hydrocephalous, or other conditions such as those described herein. Other examples where fluid can be drained into include, but are not limited to, the epidural space, including fat and/or muscle, and/or vasculature including the veins, such as the anterior and/or posterior spinal veins, vertebral bodies, soft tissue, or the like. Some embodiments are generally directed to a device defining a conduit connecting a first end to a second end, and a flow controller positioned to allow fluid (e.g., cerebrospinal fluid) to flow from the first body cavity through the first end to the second end and into a second body cavity (e.g., peritoneum). In some embodiments, the device may be implanted, e.g., via percutaneous injection, at any location along or within a subject's spinal column, such as, for example, a thecal sac. In some embodiments, the device is configured and arranged to be positioned between two vertebra of a human subject. The term "thecal sac" is synonymous with dural sac, tube of dura mater, intradural intrathecal sac, and the like.

Figure 1A:
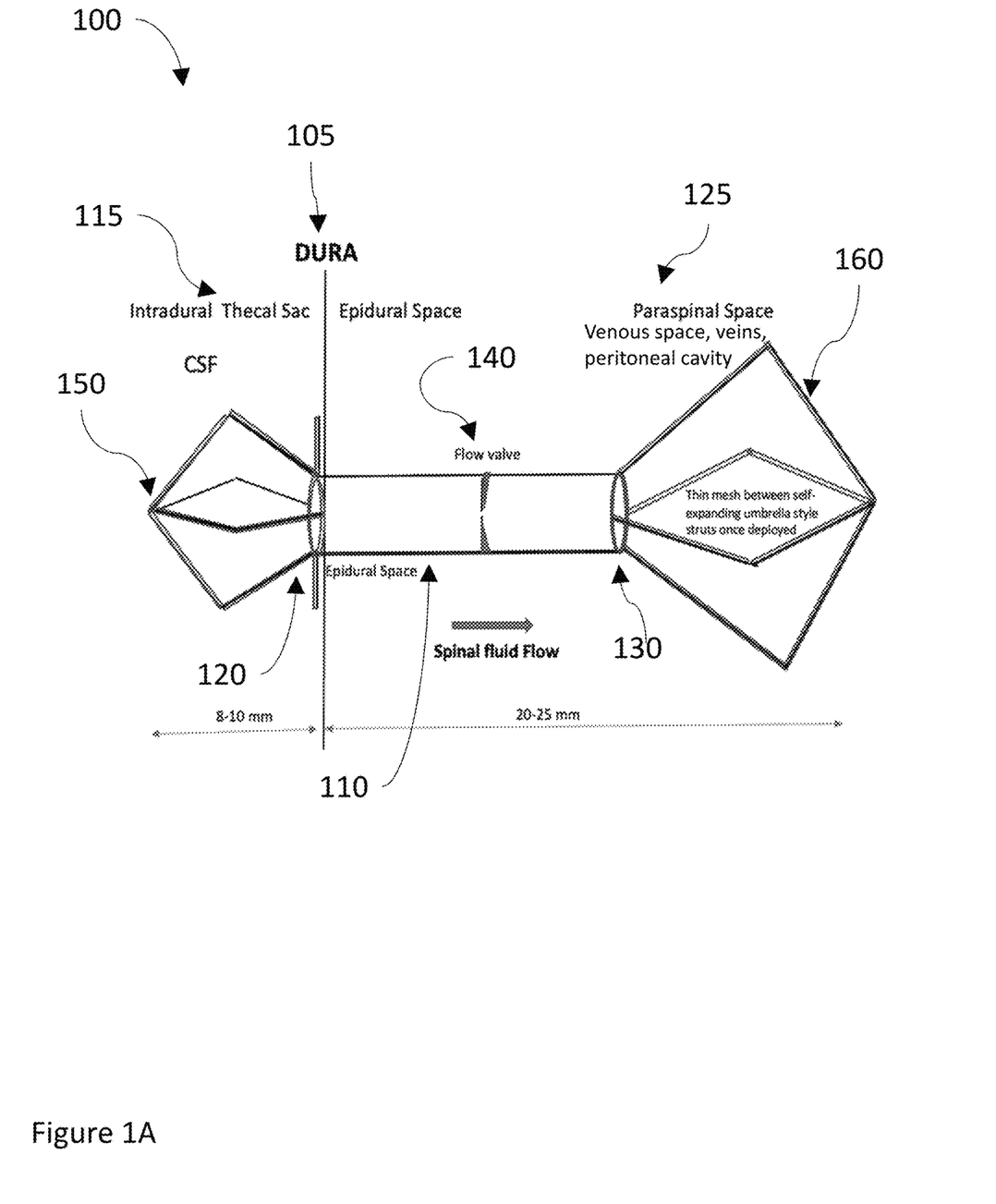
FIG. 1A is a schematic illustrating a side view of a device placing a thecal sac in fluidic communication with a paraspinal and/or venous space, according to some embodiments.
Figure 1B:
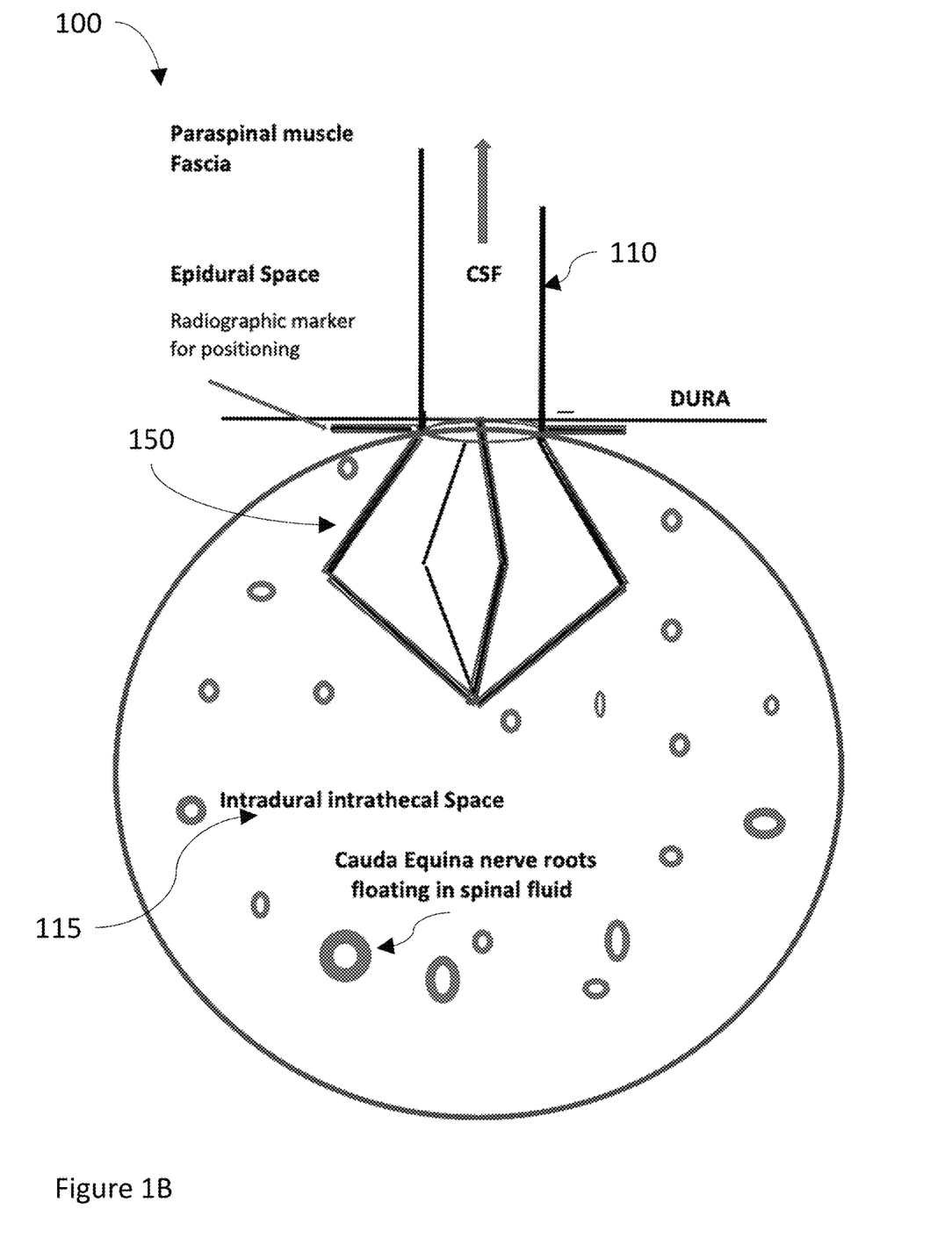
FIG. 1B is a schematic illustrating a top-view of a first end of a device implanted within a thecal sac, according to some embodiments.

A non-limiting example is now provided with respect to FIG. 1A, which illustrates a side view of an exemplary device 100 configured to drain, for example, cerebrospinal fluid from a thecal sac into a paraspinal space, epidural vein, vena cava, or peritoneal cavity. As shown in FIG. 1A, the exemplary device 100 comprises an implantable structure 110 that defines a conduit therein connecting a first end 120 to a second end 130. In some embodiments, the first end 120 is placed within the first body cavity, such as, thecal sac 115, and a first expansion apparatus 150 positioned at the first end 120 of the implantable device is expanded into an expanded configuration larger than the first end 120 of the implantable device, thus anchoring the implantable device to the first body cavity (e.g., intradural thecal sac, 115). FIG. 1B illustrates a top view of device 100 following expansion of the first expansion apparatus 150 within thecal cavity 115 (i.e., the first body cavity). The first expansion apparatus acts as an anchor to secure the implantable structure 110 to the outside of thecal cavity 115 (i.e., the first body cavity).

As shown in FIG. 1A, in some embodiments, a second end 130 of the device is placed within a second body cavity, such as paraspinal space 125, and a second expansion apparatus 160, positioned at the second end 130 of the implantable structure, is expanded into an expanded configuration larger than the second end 130 of the implantable structure 110, thus anchoring the implantable structure 110 to the second body cavity (e.g., the paraspinal space 125). In some embodiments, the device further comprises a flow controller 140 positioned within implantable structure 110 in an orientation that allows fluid (e.g., cerebrospinal fluid) to flow from the first body cavity (e.g., intradural thecal sac 115) through the first expansion apparatus 150, located at the first end 120, through the implantable device 110, through the second expansion apparatus 160, located at second end 130, and into the second body cavity (e.g., paraspinal space, venous space, vertebral body 125).

As described above, in some embodiments, a device may comprise a first expansion apparatus positioned at a first end, configured to expand within a first body cavity to anchor the device to a surrounding tissue. In some embodiments, the first expansion apparatus, prior to expansion, has a collapsed configuration smaller than the first end of the device. In other embodiments, the first expansion apparatus is at least partially contained within the first end of the conduit prior to expansion. In some embodiments, the first expansion apparatus, when fully expanded, has a maximum cross-sectional dimension of between 0.5-2.0 mm and a length of between 1.0-15.0 cm depending on placement within the conduit.

Figures 2A, 2B:
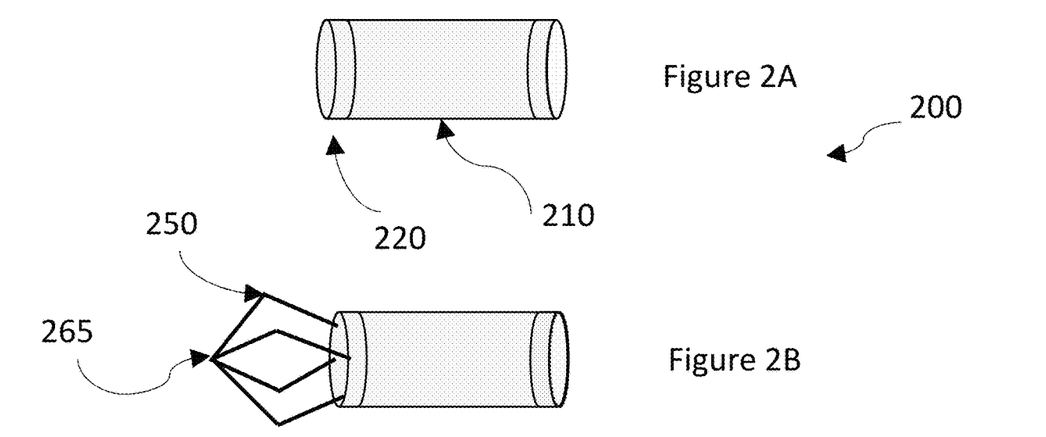
FIG. 2A is a schematic illustrating a side view of a device comprising an implantable structure defining a first end, according to some embodiments.
FIG. 2B is a schematic illustrating a side view of a device comprising a first expansion apparatus comprising a plurality of first hinged arms in an expanded geometry, according to some embodiments.
Figure 2C:
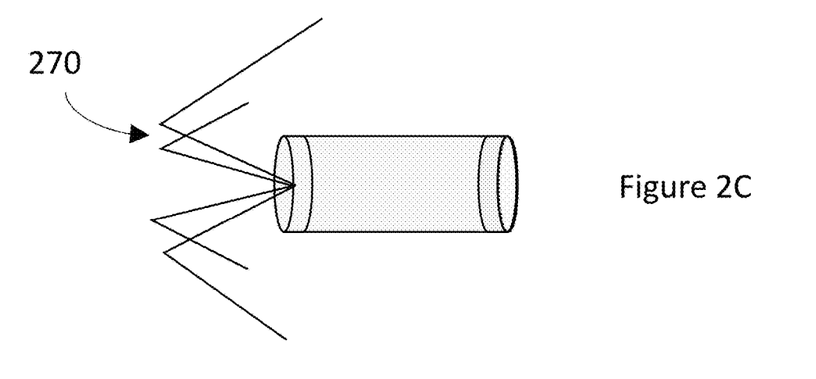
FIG. 2C is a schematic illustrating a side view of a device comprising a first expansion apparatus comprising a plurality of first hinged arms with grapnel geometry, according to some embodiments.

An expansion apparatus may comprise any shape and/or geometry capable of securing an implantable device within a first body cavity. FIGS. 2A-2E illustrate various exemplary embodiments of a device 200, with various expansion apparatuses. Other apparatuses are also possible besides these examples. In FIG. 2A, the device includes an implantable structure 210 that defines a conduit therein connecting a first end 220 to a second end. In the embodiment shown in FIG. 2B, the expansion apparatus 250 comprises a plurality of hinged arms with an expanded geometry. In some cases, the plurality of hinged arms each connect a point on the first end 220 of the conduit to a first common point 265. The number of arms can vary; for example, in some embodiments, the plurality of first hinged arms comprises at least 2 hinged arms, at least 3 hinged arms, at least 4 hinged arms, at least 5 hinged arms, at least 6 hinged arms, etc. In addition, the arms may not all necessarily be hinged and/or the arm may not necessarily connect to a common point. For example, in the embodiment shown in FIG. 2C, the expansion apparatus 270 comprises a plurality of hinged arms with a grapnel geometry configured to physically tether the device to the surrounding tissue. Unlike FIG. 2B, in FIG. 2C, the arms do not connect to a common point. In some embodiments, one or more of the arms may comprise an anchoring element, such as a barb, a hook, or the like. However, in some cases, no anchoring elements may be present. In addition, although hinged arms are shown in FIGS. 2B and 2C, it should be noted that in other embodiments, one or more of the arms may not necessarily be hinged. In addition, in some embodiments, the expansion apparatus further comprises a mesh netting spanning between at least two of the arms.

In some embodiments, one or more of the arms may comprise or be formed from a polymer. Non-limiting examples include medical grade ABS, acetal copolymer, acetal homopolymer (e.g., Delrin®), polyethylene terephthalate polyester (PET-P), mica-filled polytetrafluroroethylene (e.g., Fluorosint®), ethylene-chlorotrifluoro-ethylene (e.g., Halar®), polybutylene terephthalate-polyester (e.g., Hydex®), polyvinylidene fluoride (e.g., Kynar®), polyphenylene oxide (e.g., Noryl®), nylon, polyetheretherketone (PEEK), polycarbonate, polyethylenes (e.g., LDPE, HDPE, and UHMW), polypropylene homopolymer, polyphenylsulfone (PPSU), polysulfone (PSU), polyethersulfone (e.g., Radel® A), polyarylethersulfone (e.g., Radel® R), Rulon® 641, etc. In some embodiments, one or more of the arms may comprise or be formed of a metal and/or alloy such as medical grade metals and/or metal alloys including stainless steel, copper, titanium, cobalt chrome, aluminum, magnesium, etc. In addition, it should be understood that the above embodiments are non-limiting and that other materials are possible.

Figure 2D:
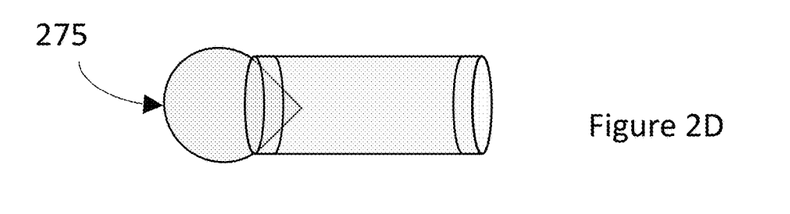
FIG. 2D is a schematic illustrating a side view of a device comprising a first expansion apparatus comprising a first expandable balloon, according to some embodiments.
Figure 2E:
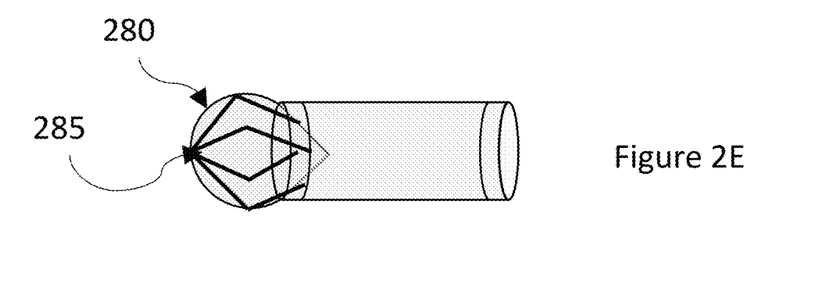
FIG. 2E is a schematic illustrating a side view of a device comprising a first expansion apparatus comprising a first expandable balloon comprising a plurality of second hinged arms in an expanded geometry, according to some embodiments.

As another non-limiting example of an expansion apparatus, in the embodiment shown in FIG. 2D, the expansion apparatus 275 comprises an expandable balloon. In some embodiments, the expandable balloon has an aspect ratio of from 0.1:1 to 1:0.1 when in the expanded configuration, where the aspect ratio is the ratio of the balloon's major axis to its minor axis (e.g., a balloon with an aspect ratio of 1:1 is spherical). In some embodiments, the expandable balloon as an aspect ratio of at least 0.1:1, of at least 0.2:1, of at least 0.3:1, of at least 0.4:1, of at least 0.5:1, of at least 0.6:1, of at least 0.7:1, of at least 0.8:1, of at least 0.9:1, of at least 1:1, of at least 0.9:1, of at least 0.8:1, of at least 0.7:1, of at least 0.6:1, of at least 0.5:1, of at least 0.4:1, of at least 0.3:1, of at least 0.2:1, and of at least 0.1:1. In some embodiments, the aspect ratio of the expandable balloon is 1:1.

In some embodiments, an expandable balloon comprises one or more protruding spikes to increase flow of spinal fluid, for example, by preventing adjacent tissues from blocking entry (i.e., a first end) and exit channels (i.e., a second end). In some embodiments, the spikes may have a plurality of pores at their base for spinal fluid flow. In other embodiments, the spikes may be used to help anchor the balloon within a subject.

In some embodiments, the expandable balloon comprises a plurality of pores. The expandable balloon may also have a variety of suitable porosities (i.e., pore densities). The porosity of the material forming the walls of the expandable balloon of may be greater than or equal to 40 vol %, greater than or equal to 50 vol %, greater than or equal to 60 vol %, greater than or equal to 70 vol %, greater than or equal to 80 vol %, or greater than or equal to 90 vol %. The porosity may also be less than or equal to 95 vol %, less than or equal to 90 vol %, less than or equal to 80 vol %, less than or equal to 70 vol %, less than or equal to 60 vol %, or less than or equal to 50 vol %. Combinations of the above-referenced ranges are also possible (e.g., greater than or equal to 40 vol % and less than or equal to 95 vol %, greater than or equal to 60 vol % and less than or equal to 95 vol %, or greater than or equal to 80 vol % and less than or equal to 95 vol %). Other ranges are also possible.

In some embodiments, the balloon may have a variety of suitable pore sizes. In some embodiments, the median pore size may be greater than or equal to 10 microns, greater than or equal to 12 microns, greater than or equal to 14 microns, greater than or equal to 16 microns, or greater than or equal to 18 microns. In some embodiments, the pores may have a median pore size of less than or equal to 20 microns, less than or equal to 18 microns, less than or equal to 16 microns, less than or equal to 14 microns, or less than or equal to 12 microns. Combinations of the above-referenced ranges are also possible (e.g., greater than or equal to 10 microns and less than or equal to 20 microns). Other ranges are also possible.

In another exemplary embodiment, an expansion apparatus may comprise any combination of the above referenced geometries, and/or other geometries. For example, in the embodiment shown in FIG. 2E, the expansion apparatus 280 comprises a first expandable balloon and a plurality of hinged arms.

Figure 3A:
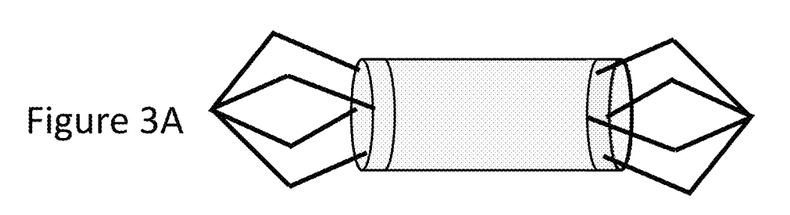
FIG. 3A is a schematic illustrating a side view of a device shown in FIG. 2B further comprising a second expansion apparatus comprising a plurality of third hinged arms in an expanded geometry, according to some embodiments.
Figure 3B:
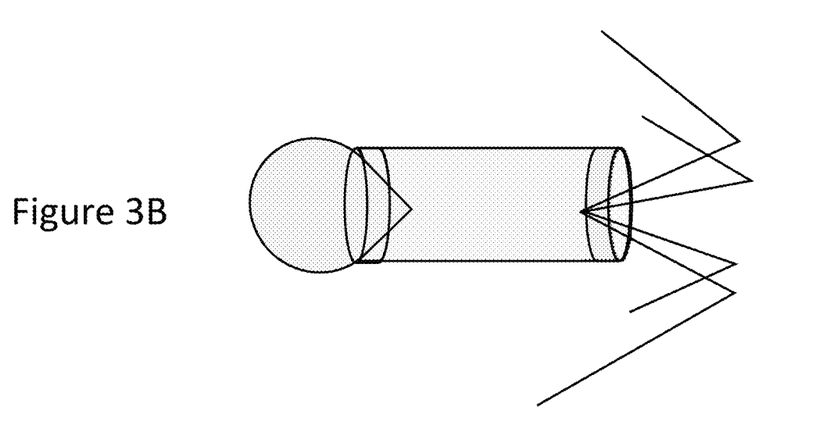
FIG. 3B is a schematic illustrating a side view of a device shown in FIG. 2D further comprising a second expansion apparatus comprising a plurality of third hinged arms with grapnel geometry, according to some embodiments.

As described above, in some embodiments, a device may comprise more than one expansion apparatus, for example, a first expansion apparatus and a second expansion apparatus. If more than one expansion apparatus is present, they may independently be the same or different. Non-limiting examples of such devices include those shown in FIGS. 3A and 3B. FIG. 3A illustrates an embodiment where a device has two substantially identical expansion apparatuses, while in FIG. 3B, the two expansion apparatuses are different.

In some embodiments, exemplary devices comprise a flow controller. The flow controller may regulate the volumetric flow rate and/or direction, etc. of fluid flow from the first body cavity. In some cases, the flow controller may reduce or prevent backflow from the second body cavity, or other location where fluid can be drained, e.g., as discussed herein. In certain cases, the flow controller is physically coupled to the device e.g., to a conduit inside the device. In some embodiments, the flow controller may be located at any location within the conduit. For example, in some cases, the flow controller is located between 5-40 mm from the first end. In some embodiments, the flow controller is located greater than or equal to 5 mm, greater than or equal to 10 mm, greater than or equal to 20 mm, greater than or equal to 30 mm, and greater than or equal to 40 mm from the first end. In some embodiments, the flow controller is located at less than or equal to 40 mm, less than or equal to 30 mm, less than or equal to 20 mm, less than or equal to 10 mm, and less than or equal to 5 mm from the first end.

A variety of flow controllers may be used in various embodiments. For instance, in some embodiments, the flow controller may comprise a valve. Any of a variety of valves may be used in different embodiments, for example, a gate valve, a butterfly valve, a knife gate valve, a globe valve, a needle valve, a pinch valve, etc.

In some embodiments, the valve is a one-way check valve. A one-way valve is a valve that normally allows fluid (e.g., cerebrospinal fluid) to preferentially flow through it in only one direction, compared to the reverse direction. Some exemplary one-way check valves include, but are not limited to, a ball check valve, a diaphragm check valve, a swing check valve, a titling disk check valve, a flapper valve, a clapper valve, a backwater valve, a stop-check valve, a lift-check valve, an in-line valve, a duckbill valve, a pneumatic non-return valve, a reed valve, a flow check valve, a capillary valve, and the like.

In some cases, a one-way valve may be described by a characteristic cracking pressure, which is the minimum differential upstream pressure between the inlet (i.e., the first body cavity) and the outlet (e.g., the second body cavity or other location where fluid can be drained, e.g., as discussed herein) at which the valve will operate. In some embodiments, the characteristic cracking pressure of the one-way valve is between 20-75 mmH$_2$O. In some embodiments, the cracking pressure of the one-way valve is greater than or equal to 20 mmH$_2$O, greater than or equal to 25 mmH$_2$O, greater than or equal to 35 mmH$_2$O, greater than or equal to 45 mmH$_2$O, greater than or equal to 55 mmH$_2$O, and greater or equal to 75 mmH$_2$O. In some embodiments, the cracking pressure of the one-way valve is less than or equal to 75 mmH$_2$O, less than or equal to 55 mmH$_2$O, less than or equal to 45 mmH$_2$O, less than 35 mmH$_2$O, less than or equal to 25 mmH$_2$O, and less than or equal to 20 mmH$_2$O.

In some embodiments, a device comprising a one-way valve may drain fluid from a first body cavity to a second body cavity, e.g., when the pressure in the first body cavity rises above a cracking pressure (i.e., the opening pressure). For example, placement of a device into a thecal cavity, where the intrathecal pressure is greater than the cracking pressure of the one-way valve, may open the valve and allow fluid to drain from the intrathecal space to the second body cavity, or other location where fluid can be drained, e.g., until the intrathecal pressure reaches the cracking pressure, at which point the one-way valve may close to stop fluid transfer.

In one set of embodiments, some of the devices described herein may have a shape suitable for implantation, for example, by insertion with a needle such as is described herein. The implant may have a shape such as hollow cylinders, or hollow ellipsoids, etc. The implant may have any cross-sectional shape, e.g., circular, angular, elliptical, or the like. In some cases, the implant may have a constant cross-sectional shape and/or constant cross-sectional dimensions, e.g., as in a cylindrical profile.

In some embodiments, the device has a length of between 1.0 cm and 15.0 cm. In some embodiments, the length of the device may be greater than or equal to 1 cm, greater than or equal to 5, greater than or equal to 10 cm, and greater than or equal to 15 cm. In some embodiments, the device may have a length that is less than or equal to 15 cm, less than or equal to 10 cm, is less than or equal to 5 cm, and less than or equal to 1 cm.

In some embodiments, the device may have an internal diameter of between 1.0 mm and 2.5 mm. In some embodiments, the internal diameter may be greater than or equal to 1 mm, greater than or equal to 1.5 mm, greater than or equal to 2 mm, and greater than 2.5 mm. In some embodiments, the internal diameter may be less than or equal to 2.5 mm, less than or equal to 2.0 mm, is less than or equal to 1.5 mm, and less than or equal to 1.0 mm.

In some embodiments, the device may have an outer diameter of 2.0-3.5 mm. In some embodiments, the wall thickness may be greater than or equal to 2.0 mm, greater than or equal to 2.5 mm, greater than or equal to 3 mm, and greater than 3.5 mm. In some embodiments, the wall thickness may be less than or equal to 3.5 mm, less than or equal to 3.0 mm, is less than or equal to 2.5 mm, and less than or equal to 2.0 mm.

In some embodiments, the device may have a maximum cross-sectional dimension of between 3.0 mm and 6.0 mm. In some embodiments, the maximum cross-sectional dimension may be greater than or equal to 3 mm, greater than or equal to 4 mm, greater than or equal to 5 mm, and greater than or equal to 6 mm. In some embodiments, the maximum cross-sectional dimensions may be less than or equal to 6 mm, less than or equal to 5 mm, is less than or equal to 4 mm, and less than or equal to 3 mm.

The device may comprise or be formed from any suitable material. In some embodiments, the material is a medical grade polymer, metal, and/or metal alloy. Non-limiting exemplary embodiments of medical grade polymers include silicon, ABS, acetal copolymer, acetal homopolymer (e.g., Delrin®), polyethylene terephthalate polyester (PET-P), mica-filled polytetraflurorethylene (e.g., Fluorosint®), ethylene-chlorotrifluoro-ethylene (e.g., Halar®), polybutylene terephthalate-polyester (e.g., Hydex®), polyvinylidene fluoride (e.g., Kynar®), polyphenylene oxide (e.g., Noryl®), nylon, polyetheretherketone (PEEK), polycarbonate, polyethylenes (e.g., LDPE, HDPE, and UHMW), polypropylene homopolymer, polyphenylsulfone (PPSU), polysulfone (PSU), polyethersulfone (e.g., Radel® A), polyarylethersulfone (e.g., Radel® R), Rulon® 641, etc. Exemplary embodiments of medical grade metals and/or metal alloys include, but are not limited to, stainless steel, copper, titanium, cobalt chrome, aluminum, magnesium, etc. It will be understood that the above embodiments are non-limiting and that other embodiments are possible. For example, in some embodiments, the implantable structure may comprises a combination of medical grade polymers, metals, and/or alloys, etc.

In some embodiments, the device may comprise a coating. A coating may be useful, for example, for reducing infection, immune rejection or reaction to the device. In some embodiments, the coating comprises a non-water-soluble polymer, such as a thin polymer film. In certain embodiments, the coating comprises a hydrogel. In another exemplary embodiment, the coating comprises alternating layers of oppositely charged polymers (e.g., poly-L-lysine and poly-glutamic acid). In some embodiments, the coating may comprise diamond like carbon coatings (DLC) and/or biocompatible electrostimulation coatings such as titanium nitride (TiN) and/or sputtered iridium oxide (IrOx).

In some embodiments, the coating may comprise one or more therapeutic compounds. In some embodiments, the therapeutic compound may comprise an antimicrobial compound, for example, to prevent infection following implantation of the device within a subject. In some embodiments, the antimicrobial compound comprises a penicillin. Non-limiting examples include penicillin V, penicillin G, amoxicillin, amoxicillin/clavulonate, ampicillin, nafcillin, oxacillin, dicloxacillin, piperacillin, pipercillin/tazobactam, and the like. In some embodiments, the antimicrobial compound comprises a macrolide. Examples include, but are not limited to, azithromycin, clarithromycin, fidaxomicin, erythromycin, telithromycin, and the like. In some embodiments, the antimicrobial compound comprises a cephalosporin. Examples include, but are not limited to, cefacetril, cefradin, cefroxadin, cefaloglycin, cefaclor, cefalexin, cefadroxil, cefatrizin, cefazedon, cefapirin, ceftezol, cefazolin, cefazaflur, cefalotin, cefaloridin, cefalonium, and the like. In some embodiments, the antimicrobial compound comprises a fluoroquinolone. Examples include balofloxacin, grepafloxacin, levofloxacin, pazufloxacin, sparfloxacin, temafloxacin, clinafloxacin, gatifloxacin, moxifloxacin, sitafloxacin, prulifloxacin, besifloxacin, delafloxacin, and the like. In some embodiments, the antimicrobial compound comprises a beta-lactam. Examples include penams, carbapenams, clavams, penems, carbapenems, cephems, carbacephems, oxacephems, monobactams, and the like. Combinations are also possible (e.g., the coating may comprise a penicillin and a beta-lactam or a fluoroquinolone and a cephalosporin, etc.).

In some embodiments, a therapeutic compound may comprise an anti-proliferative compound to prevent, for example, a surrounding tissue from growing inside a conduit defined by an implantable structure (i.e., to prevent a device from becoming plugged). Exemplary embodiments of anti-proliferative compounds include mycophenolate mofetil, mycophenolate sodium, azathioprine, sirolimus, paclitaxel, etc.

Figure 4:
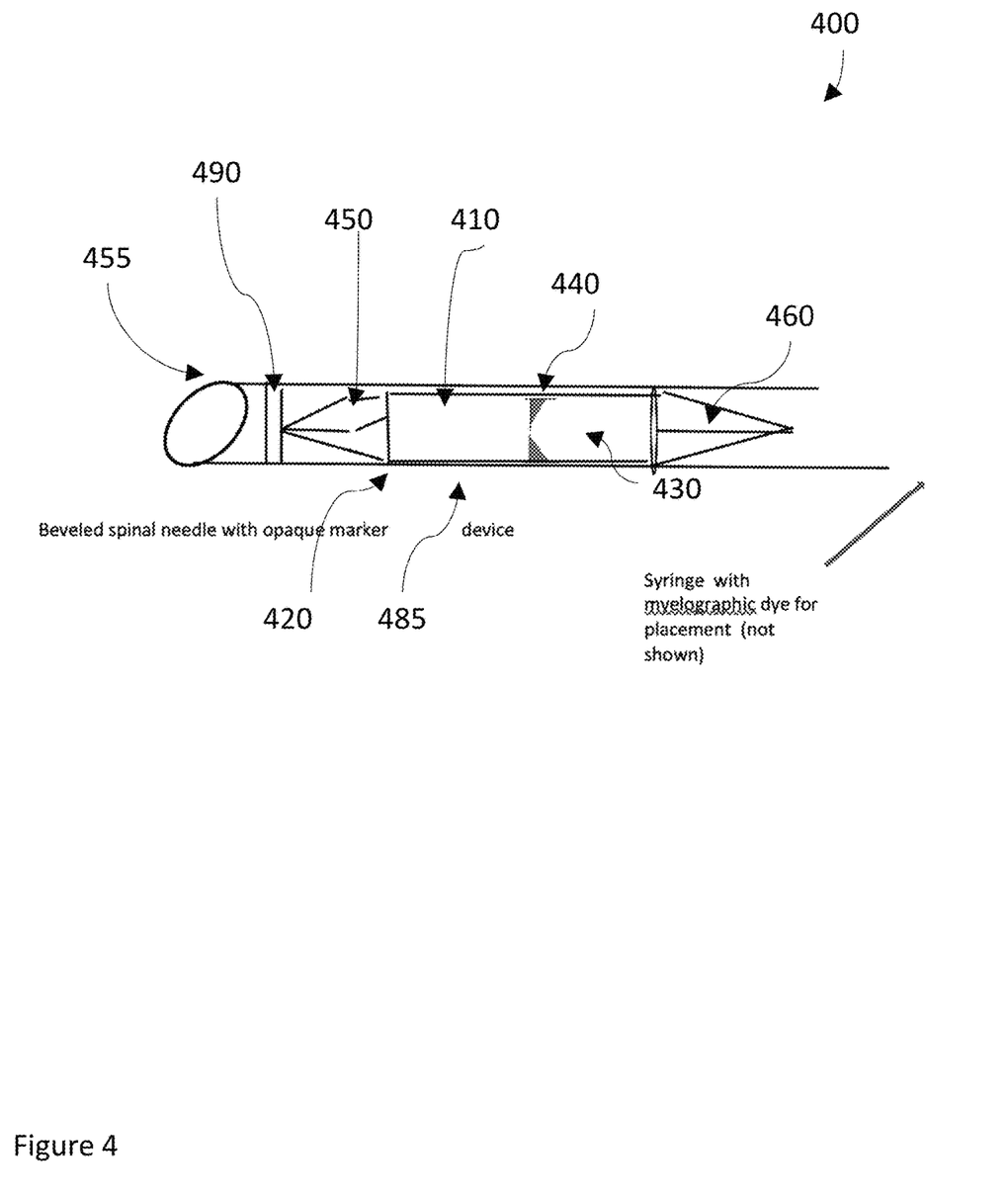
FIG. 4 is a schematic illustrating a side view of an apparatus comprising a spinal syringe and an implantable device loaded within a barrel of the spinal syringe prior to implantation; in accordance with some embodiments.

Some aspects of the disclosure relate to an apparatus that may be used, for example, to deliver a device to a subject in need thereof. An exemplary apparatus 400 is shown in FIG. 4. In this figure, apparatus 400 comprises a hollow needle shaft 455 having a substantially constant cross-sectional area. In some embodiments, the hollow needle shaft 455 may be part of a spinal needle, or other needle. In some embodiments, the hollow needle shaft comprises a Quincke needle tip. Quincke needles (or cutting-tip needles) have sharp cutting tips, with the hole at the end of the needle shaft (as opposed to a hole in the middle of the needle shaft). Other exemplary needles that have the hole at the end of the needle shaft include Pitkin needles (rounded, short cutting bevel at needle tip), Greene needles (tapered non-cutting bevel at the needle tip), and Tuohy needles (very slightly curved at needle tip). Other needles and needle tips may be used in other embodiments.

In FIG. 4, exemplary apparatus 400 comprises a device 485, wherein the device 485 is at least partially contained within the hollow shaft of the needle 455. The device in FIG. 4 may also comprise an implantable structure 410 defining a conduit therein connecting a first end 420 to a second end 430. Device 485 may also comprise a flow controller 440 (e.g., a one-way valve) positioned within the implantable structure in an orientation that allows fluid to flow through the conduit from the first end 420 to the second end 430. Exemplary device 400 may also comprise a first expansion apparatus 450 positioned at the first end 420 of the implantable structure 410, wherein the first expansion apparatus 450 has a collapsed configuration smaller than the first end 420 and is at least partially contained within the first end 420 of the conduit. As shown in FIG. 4, exemplary device 400 may also comprise a second expansion apparatus 460 positioned at the second end 430 of the implantable structure 410, wherein the second expansion apparatus 460 has a collapsed configuration smaller than the second end 430 and is at least partially contained within the second end 430 of the conduit. In some embodiments, the first expansion apparatus 450 and second expansion apparatus 460, when removed from the hollow needle shaft (e.g., during implantation), are expandable into a configuration larger than the cross-sectional area of the hollow needle shaft, e.g., as described herein. For example, in some embodiments, removing the first end and/or second end of the device from the hollow needle shaft causes the first expansion apparatus and second expansion apparatus to expand into an expanded configuration. In other embodiments, the first expansion apparatus and/or second expansion apparatus may be triggered to expand using an external triggering mechanism, such as temperature, light, ultrasound, magnetic fields, electric fields, etc.

In some embodiments, the needle shaft may comprise an opaque maker to aid in placement, for example, using fluoroscopy, CT scan, ultrasound, etc. Examples of radio-opaque markers include, but are not limited to, iodine, barium, tantalum, tungsten, rhenium, osmium, iridium, noble metals, palladium, platinum, gold, silver, bismuth, etc. In some embodiments, the radio-opaque marker is a transition metal. In some cases, the radio-opaque marker may be present as an oxide.

Certain aspects of the disclosure relate to systems and methods of inserting a device in a subject in need thereof (e.g., for the treatment of hydrocephalous or other conditions). In some embodiments, the device may be configured to drain fluid from a first body cavity (e.g., spinal canal) to a second body cavity (e.g., peritoneum, epidural space, including fat and/or muscle, and/or vasculature including the veins, such as the anterior and/or posterior spinal veins, vertebral bodies, soft tissue, or the like). For example, in some embodiments, the subject has a thecal sac containing an excess of cerebrospinal fluid.

In some embodiments, a hollow needle (e.g., a spinal needle) having a substantially constant cross-sectional area and an implantable device at least partially contained within the hollow shaft may be applied to a subject. In some embodiments, an apparatus such as a needle may be used to deliver the device. For example, the device to be implanted may be contained within the shaft of a needle, which can be inserted into the subject to administer the device. For example, the device may be implanted to the spinal column of the subject. In some embodiments both radiographic and endoscopic techniques may be used to confirm correct location.

In some embodiments, a hollow needle shaft comprising a device such as discussed herein is placed or inserted into a first body cavity, and expanding a first expansion apparatus into a configuration larger than a first end of the device. In addition, in certain embodiments, the hollow needle shaft may be injected into a thecal sac (or other first body cavity) of the subject and expanding the first expansion apparatus into a configuration larger than the first end of the device. Any mechanism of expanding the first expansion apparatus, such as temperature, light, ultrasound, magnetic fields, electric fields, etc., may be used for triggering the expansion of the first expansion apparatus. For example, in some embodiments, a spring-loaded mechanism may be used for expanding a plurality of first hinged arms into an expanded configuration. Similarly, as another example, air pressure may be applied (e.g., through the needle shaft), for example, to expand an expandable balloon. In some embodiments, expanding the first expansion apparatus anchors the device to the thecal sac.

In some embodiments, a hollow needle shaft may be at least partially withdrawn from a subject. For example, in some embodiments, partially withdrawing the hollow needle shaft from the subject moves the hollow needle shaft from a thecal sac into an extradural space. In other embodiments, completely withdrawing the hollow needle shaft from the subject causes a device to fully exit the hollow needle shaft. In some embodiments, removing the device from the hollow needle shaft expands a second expansion apparatus into a configuration larger than a second end of the device. Any mechanism of expanding the second expansion apparatus, such as temperature, light, ultrasound, magnetic fields, electric fields, etc., may be used for triggering the expansion of the second expansion apparatus. For example, in some embodiments, a spring-loaded mechanism may be used for expanding a plurality of second hinged arms into an expanded configuration. Similarly, as another example, air pressure may be applied, for example, to expand a second expandable balloon. In some embodiments, expanding the second expansion apparatus anchors the device to the extradural space.

In some embodiments, a device such as described herein may be inserted or implanted between a first body cavity and a second body or other location where fluid can be drained, e.g., as discussed herein, thus permitting fluid to flow from the first body cavity into the second body cavity via the device. In some embodiments, the first body cavity comprises a thecal sac and the second body cavity an extradural space or paraspinal vein. In some embodiments, anchoring the device between the thecal sac and the extradural space allows the extradural space to receive excess cerebrospinal fluid from the thecal sac. In some embodiments, the device may further comprise a catheter, for example, to transport the fluid to a space distant from the first body cavity. For example, in some embodiments, the method comprising tunneling the catheter from the second end of the implantable device positioned in a paraspinal space to a peritoneal cavity, such that that the peritoneal cavity may receive the cerebrospinal fluid from the thecal sac.

A variety of techniques may be used to gain access to the implantation site, e.g., within the spinal column, for example, within the spinal canal or vertebral body. As non-limiting examples, the device may be inserted via a minimally invasive procedure, such as percutaneous administration. In one set of embodiments, an open approach may be used, e.g., where access is gained through laminotomy or laminectomy to access intradural space. In another set of embodiments, a minimally invasive intrathecal procedure may be used to gain access to the implantation site, e.g., to allow for the insertion of the device. Those of ordinary skill in the art will be familiar with techniques such as laminotomy or laminectomy. In addition, in some embodiments, the device may be inserted so it acts as a lumbar drain.

U.S. Provisional Patent Application Ser. No. 63/337,019, filed Apr. 29, 2022, entitled "Systems and Methods for Draining Cerebrospinal Fluid," by Meyer, et al., is incorporated herein by reference in its entirety.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for percutaneous spinal delivery of a device, the apparatus comprising:
    a needle sized to percutaneously inject the device into the spine of the subject, the needle comprising a hollow needle shaft at least partially containing the device, wherein the device comprises:
        an implantable structure defining a conduit therein connecting a first end to a second end;
        a flow controller positioned within the implantable structure in an orientation that allows spinal fluid to flow through the conduit from the first end to the second end;
        a first expansion apparatus positioned at the first end of the implantable structure, wherein the first expansion apparatus is expandable into an expanded configuration larger than the first end; and
        a second expansion apparatus positioned at the second end of the implantable structure, wherein the second expansion apparatus is expandable into an expanded configuration larger than the second end.

2. The apparatus of claim 1, wherein the first expansion apparatus, prior to expansion, has a collapsed configuration smaller than the first end.

3. The apparatus of claim 1, wherein the first expansion apparatus is at least partially contained within the first end of the conduit prior to expansion.

4. The apparatus of claim 1, wherein the first expansion apparatus comprises a plurality of first hinged arms.

5. The apparatus of claim 1, wherein the first expansion apparatus further comprises a first mesh netting spanning between at least two of the plurality of first hinged arms.

6. The apparatus of claim 1, wherein the first expansion apparatus comprises a first expandable balloon.

7. The apparatus of claim 1, wherein the second expansion apparatus, prior to expansion, has a collapsed configuration smaller than the second end.

8. The apparatus of claim 1, wherein the second expansion apparatus is at least partially contained within the second end of the conduit prior to expansion.

9. The apparatus of claim 1, wherein the flow controller comprises a one-way valve.

10. The apparatus of claim 1, wherein the implantable structure is configured and arranged to be positioned between two vertebrae of a human subject.

11. The apparatus of claim 1, wherein the first expansion apparatus is spontaneously expandable.

12. The apparatus of claim 1, wherein the second expansion apparatus is spontaneously expandable.

13. The apparatus of claim 10, wherein the implantable structure is configured and arranged to be positioned between two vertebrae of a human subject, connecting the intrathecal sac to an epidural space within the human subject.

14. An apparatus for spinal delivery of a device, the apparatus comprising:
    a spinal needle comprising a hollow needle shaft having a substantially constant cross-sectional area, wherein the spinal needle is sized to percutaneously inject the device into the spine of a human subject; and
    a device at least partially contained within the hollow shaft of the spinal needle, the device comprising:
        an implantable structure defining a conduit therein connecting a first end to a second end;

a flow controller positioned within the implantable structure in an orientation that allows fluid to flow through the conduit from the first end to the second end;
a first expansion apparatus positioned at a first end of the implantable structure, wherein the first expansion apparatus, when removed from the hollow needle shaft, is expandable into a configuration larger than the cross-sectional area of the hollow needle shaft; and
a second expansion apparatus positioned at a second end of the implantable structure, wherein the second expansion apparatus, when removed from the hollow needle shaft, is expandable into a configuration larger than the cross-sectional area of the hollow needle shaft.

15. A method of delivering an implantable structure into a subject having a spinal column, the method comprising:
inserting a hollow needle shaft into an intrathecal sac of the spinal column of the subject, the hollow needle shaft having a substantially constant cross-sectional area and an implantable device at least partially contained within the hollow shaft, wherein the implantable device comprises a first expansion apparatus positioned at a first end of the implantable device, a second expansion apparatus positioned at a second end of the implantable device, and a flow controller positioned within the implantable structure in an orientation that allows fluid to flow through the conduit from the first end to the second end;
expanding the first expansion apparatus into a configuration larger than the first end;
at least partially withdrawing the needle shaft from the subject; and
expanding the second expansion apparatus into a configuration larger than the second end.

16. The method of claim 15, wherein the intrathecal sac contains an excess pressure of cerebrospinal fluid.

17. The method of claim 15 wherein partially withdrawing the hollow needle shaft from the subject moves the hollow needle shaft from the thecal sac into an extradural space.

18. The method of claim 17, further comprising completely withdrawing the hollow needle shaft from the subject.

19. The method of claim 18, wherein completely withdrawing the needle shaft from the subject completely removes the implantable device from the hollow needle shaft.

20. The method of claim 19, wherein completely removing the implantable device from the hollow needle shaft causes the second expansion apparatus to expand into a configuration larger than the second end of the implantable device.

21. The method of claim 15, wherein expanding the second expansion apparatus anchors the implantable device to the extradural space.

22. The method of claim 21, wherein anchoring the implantable structure between the thecal sac and the extradural space allows the extradural space to receive the cerebrospinal fluid from the thecal sac.

* * * * *